(12) United States Patent
Aronson (10) Patent No.: US 10,307,223 B1
(45) Date of Patent: Jun. 4, 2019

(54) TOOTH ALIGNER REMOVAL DEVICE

(71) Applicant: Ross E. Aronson, Rye Brook, NY (US)

(72) Inventor: Ross E. Aronson, Rye Brook, NY (US)

( * ) Notice: Subject to any disclaimer, the term of this patent is extended or adjusted under 35 U.S.C. 154(b) by 0 days.

(21) Appl. No.: 15/940,030

(22) Filed: Mar. 29, 2018

(51) Int. Cl.
*A61C 7/02* (2006.01)
*A61C 7/08* (2006.01)

(52) U.S. Cl.
CPC .............. *A61C 7/023* (2013.01); *A61C 7/08* (2013.01)

(58) Field of Classification Search
CPC ...................................................... A61C 7/023
See application file for complete search history.

(56) References Cited

U.S. PATENT DOCUMENTS

| 1,389,954 A | * | 9/1921 | McCombs | A61C 3/14 |
| | | | | 433/141 |
| 7,011,517 B2 | * | 3/2006 | Nicozisis | A61C 7/02 |
| | | | | 433/141 |
| 8,062,030 B2 | * | 11/2011 | Saubers | A61C 7/02 |
| | | | | 433/141 |
| 8,167,612 B2 | * | 5/2012 | DeSanti | A61C 7/02 |
| | | | | 433/141 |
| 8,182,266 B2 | * | 5/2012 | Creasman | A61C 3/00 |
| | | | | 29/270 |
| 9,687,316 B1 | * | 6/2017 | Maassarani | A61C 3/162 |

OTHER PUBLICATIONS

OrthoKey (TM), https://theorthokey.com, (2018).*
Invisalign Removal with OrthoKey, YouTube, https://www.youtube.com/watch?v=CvSCJpJ0Sj0 (Dec. 26, 2018; "Published on Oct 30, 2016").*

* cited by examiner

*Primary Examiner* — Ralph A Lewis
(74) *Attorney, Agent, or Firm* — Andrew F. Young, Esq.; Lackenbach Siegel, LLP (57) ABSTRACT

A dental tool for removing a dental aligner secured to teeth may include a first contact point that is configured to contact a biting surface of the aligner; a second contact point that is configured to contact a gumline end of the aligner; and a third contact point that is configured to contact a lateral surface of the aligner. A method of using the dental tool to remove the dental aligner from teeth is also disclosed.

20 Claims, 5 Drawing Sheets

TOOTH ALIGNER REMOVAL DEVICE

BACKGROUND

Technical Field

The present disclosure relates generally to a device for removing a dental aligner subsequent to installation.

Description of the Related Art

Orthodontics is the practice of manipulating a patient's teeth to improve the appearance and function of the teeth. Removable tooth positioning appliances (invisible braces), such as clear plastic aligners and retainers that tightly fit over teeth are commonly used in orthodontic treatments as an alternative to braces and other bonded orthodontic equipment for controlled tooth movement to a pre-determined position.

Removable tooth positioning appliances are made to be removed prior to eating and drinking, as well as prior to brushing and flossing teeth. The appliances are fabricated from a mold of the patient's teeth to facilitate prior placement and alignment of the appliances snuggly against the surfaces of the teeth. Often, the positioning appliances are configured to be placed over the entire top and/or bottom set of teeth.

The stiffness of the tooth positioning appliance and the requirement that the appliance tightly conform to the teeth of the patient makes it difficult to remove these appliances. Since it is necessary to remove the positioning appliance many times daily in the course of the patient's daily life for cleaning, dental hygiene, to eat, and removal for cosmetic purposes and replacement in the course of treatment, the removal of the appliance can be tedious.

Patients often find removing the appliances to be difficult and in many cases painful. Removal of the appliances typically requires a lever action. Conventional dental aligner removal tools can damage a patient's teeth and gums as they are wedged against the applicant and the tooth surfaces at or near the gumline. Additionally, other aligner removers apply a shearing force against composite attachments, which are small plastic projections bonded to enamel to provide increased surface area for better tooth control. This can lead to damage to the attachment or the tooth and result in delayed treatment.

Figure 1:
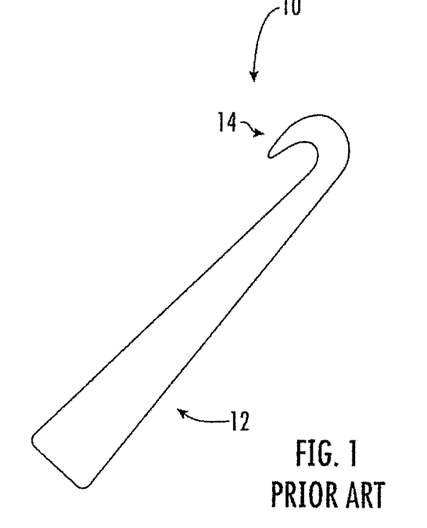
FIG. 1 is a perspective view of a conventional dental aligner removal tool.
Figure 2:
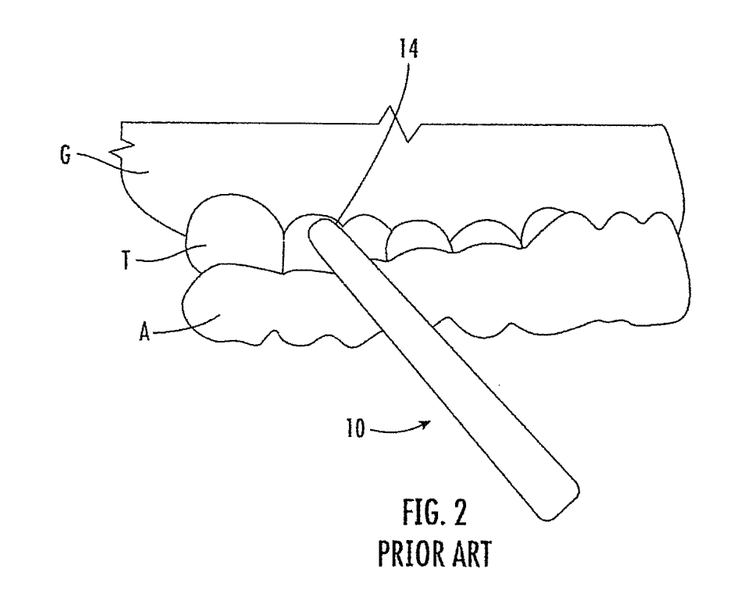
FIGS. 2, 3A, and 3B are illustrations of conventional removal methods of a dental aligner using the conventional tool of FIG. 1.

Typically, as shown in FIG. 1, a dental aligner removal tool 10 includes a handle 12 for grasping the tool and a hook 14. As shown in FIG. 2, the hook 14 of the tool 10 may be wedged between the aligner A and a surface of tooth T to wedge the hook 14 therebetween. Care must be taken not to damage the surrounding gums G. Once the hook 14 is wedged between the teeth T and the aligner A, the aligner A may be pried off the teeth T. In so doing, at least some force is necessarily applied against the teeth which is undesirable as it might cause damage to the enamel of the teeth T.

Accordingly, there is a need for new and improved tools for removing dental aligners that minimize the potential for damaging teeth and composite attachments during the removal of the aligners.

SUMMARY

The present disclosure relates to a dental tool for removing a dental aligner secured to teeth. In particular, a dental tool for removing a dental aligner secured to teeth, comprising: a first contact point that is configured to contact a biting surface of the aligner; a second contact point that is configured to a gumline end of the aligner; and a third contact point that is configured to contact a lateral surface of the aligner. Advantageously, during use, the third contact point stabilizes the tool relative to the aligner as the first contact point is in contact with the biting surface of the aligner. This allows for the tool to be pivoted relative to the third contact point while minimizing contact with any other structures within the mouth whether they be tissue or composites.

As already discussed, in an embodiment in accordance with the present disclosure, a dental tool for removing a dental aligner secured to teeth may include: a first contact point that is configured to contact a biting surface of the aligner; a second contact point that is configured to contact a gumline end of the aligner; and a third contact point that is configured to contact a lateral surface of the aligner.

In a further embodiment, a dental tool for removing a dental aligner secured to teeth may include: an elongated arm extending in a generally longitudinal direction; a generally C-shaped member disposed at a distal end of the elongated arm, the generally C-shaped member including a first member extending generally orthogonally relative to the elongated arm having a distal end and a second member spaced apart from the first member; and a protrusion extending from and disposed along the first member, the protrusion being configured to stabilize and maintain a biting surface end of the dental aligner on the first member, the first member and the second member defining a space therebetween to receive a width of the dental aligner corresponding to a length of a tooth when the dental aligner is secured to the tooth.

When the dental aligner is disposed within the space defined between the first and second members, pivoting of the elongated arm causes the distal end of the second member to exert a flexing force upon a gumline end of the aligner relative to a biting surface end of the aligner, thereby causing the aligner to separate from the teeth. The second member may define a hook curving toward the first member and may be tapered toward the distal end of the hook. The first member may define a first contact point, a distal end of the hook defines a second contact point, the protrusion defines a third contact point, the first contact point and the third contact point being configured to contact a biting end surface of the aligner, the second contact point being configured to contact a gumline end of the aligner, the third contact point being configured to inhibit slipping of the first member relative to the biting end surface of the aligner by being configured to apply a force to a lateral surface of the aligner, the second contact point being configured to engage the aligner to exert a flexing force upon the aligner when the elongated arm is pivoted relative to the third contact point. The tool may further comprise a gripping member at a proximal end of the elongated arm. The gripping member may be a ring. The tool may include a rubberized or textured surface to facilitate improved grip. For example, the distal end of the second member may be rubberized to facilitate enhanced gripping, control, and manipulation of the aligner.

A method of removing a dental aligner secured to teeth may include providing and using the tool as described above and throughout the present disclosure. In particular, the method may include providing a dental tool configured to include a first contact point that is configured to contact a biting surface of the aligner, a second contact point that is configured to contact a gumline end of the aligner, and a third contact point that is configured to contact a lateral surface of the aligner; positioning the dental tool such that the first contact point contacts the biting surface of the aligner, the second contact point contacts the gumline end of the aligner, and the third contact point contacts the lateral surface of the aligner; and pivoting the dental tool such that the second contact point rotates with respect to the third contact point. After the step of pivoting, pulling the aligner in a direction extending generally along a lateral surface of the teeth away from a gumline of a patient's mouth.

The dental tool described in the method may include: an elongated arm extending in a generally longitudinal direction; a generally C-shaped member disposed at a distal end of the elongated arm, the generally C-shaped member including a first member extending generally orthogonally relative to the elongated arm having a distal end and a second member spaced apart from the first member; and a protrusion extending from and disposed along the first member, the protrusion being configured to stabilize and maintain a biting surface end of the dental aligner on the first member, the first member and the second member defining a space therebetween to receive a width of the dental aligner corresponding to a length of a tooth when the dental aligner is secured to the tooth, wherein when the dental aligner is disposed within the space defined between the first and second members, pivoting of the elongated arm causes a distal end of the second member to exert a flexing force upon a gumline end of the aligner relative to a biting surface end of the aligner, thereby causing the aligner to separate from the teeth. The second member may define a hook curving toward the first member. The tool may exert a flexing force that is concentrated on the aligner and any force upon any surrounding mouth structure is minimized. The dental tool may further include: a gripping member at a proximal end of the elongated arm. The gripping member may be a ring. During use, a finger may be received within the ring. The tool may include a rubberized surface to facilitate improved grip. Further, at least one of the first, second, and third contact points may be rubberized.

The above and other aspects, features and advantages of the present disclosure will become apparent from the following description read in conjunction with the accompanying drawings, in which like reference numerals designate the same elements.

BRIEF DESCRIPTION OF THE DRAWINGS

A further understanding of the present disclosure can be obtained by reference to a preferred embodiment set forth in the illustrations of the accompanying drawings. Although the illustrated preferred embodiment is merely exemplary of methods, structures and compositions for carrying out the present disclosure, both the organization and method of the disclosure, in general, together with further objectives and advantages thereof, may be more easily understood by reference to the drawings and the following description. The drawings are not intended to limit the scope of this disclosure, which is set forth with particularity in the claims as appended or as subsequently amended, but merely to clarify and exemplify the disclosure.

For a more complete understanding of the present disclosure, reference is now made to the following drawings in which.

DETAILED DESCRIPTION

As required, a detailed illustrative embodiment of the present disclosure is disclosed herein. However, techniques, systems, compositions and operating structures in accordance with the present disclosure may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present disclosure.

Reference will now be made in detail to several embodiments of the disclosure that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the disclosure in any manner.

Throughout this description, tools in accordance with the present disclosure for removing dental aligners that have been secured to the surfaces of teeth will be described. To aid in understanding the advantages of the presently disclosed tools over the conventional art, an explanation of conventional means and tools for removing such aligners is also provided.

As discussed above, FIG. 1 illustrates a prior art dental aligner removal tool 10 that includes a handle 12 for grasping the tool and a hook 14. As shown in FIG. 2, the hook 14 of the tool 10 may be wedged between the aligner A and a surface of tooth T to wedge the hook 14 therebetween. Care must be taken not to damage the surrounding gums G. Once the hook 14 is wedged between the teeth T and the aligner A, the aligner A may be pried off the teeth T. In so doing, at least some force is necessarily applied against the teeth which is undesirable as it might cause damage to the enamel of the teeth T. Moreover, the motion of the tool 10 is uncontrolled because there is no stable pivot point or purchase point for the tool 10 to contact as the tool 10 is used. Instead, the tool 10 is moved in an uncontrolled fashion in the line of pull after the aligner is unseated from the surface of the teeth. This risks damage to the surrounding oral soft tissues, the hand and fingers, and the aligner itself. Advantageously, the present disclosure provides a removal tool that provides at least one purchase or pivot point (i.e., at a contact point between the tool and the aligner) thereby minimizing movement of the tool with respect to the aligner and focusing forces on the aligner as opposed to any surrounding tooth or dental structures in the patient's mouth.

Figure 3A:
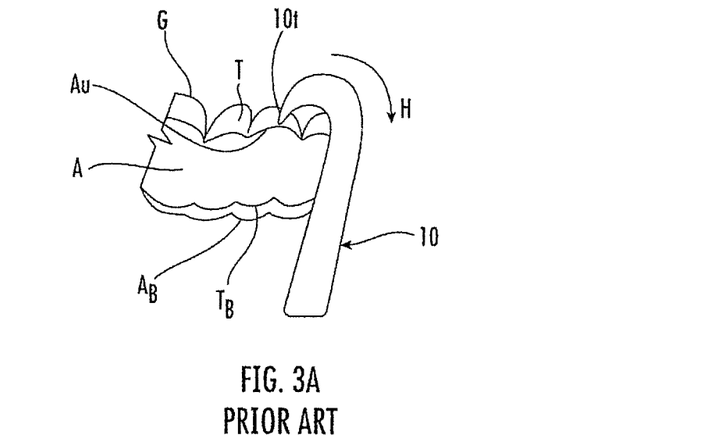
Figure 3B:
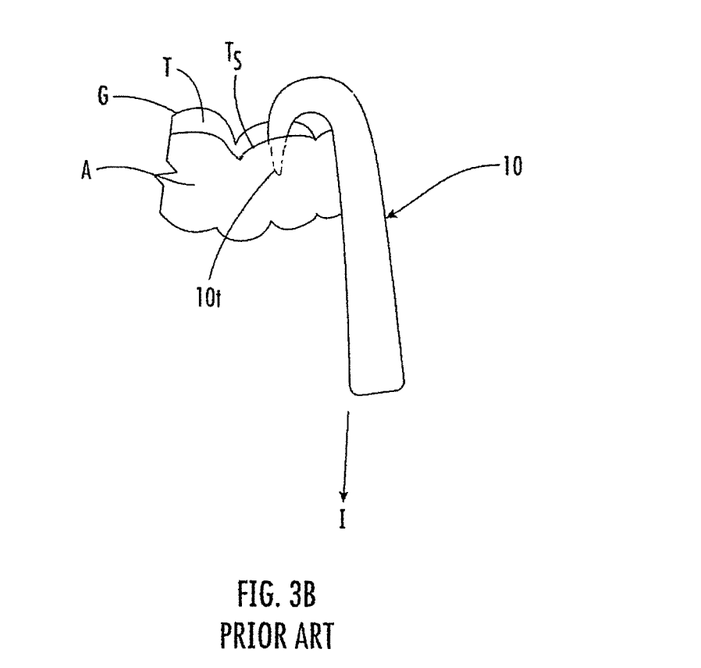

With reference to FIGS. 3A-3B, some of the disadvantages of using the conventional removal tool 10 are further described. In particular, as shown in FIG. 3A, removal of the aligner A is accomplished by placing the hook end 10t of the removal tool 10 against the gumline end surface Au of the aligner A which is at or near the gumline G. The aligner A may be wedged off the tooth T by forcing the removal tool 10 to be positioned between the surface $T_s$ of the tooth T and pulling the removal tool 10 along direction I generally parallel to the tooth surface $T_s$ and away from the gumline G. As the motion is uncontrolled, since a pivot point or purchase point is not conventionally provided, the aligner, tool and arm of the operator move in an uncontrolled fashion in the line of pull after the aligner is unseated from the surface of the teeth. This risks damage to the surrounding oral soft tissues, the hand and fingers, and the aligner itself. Importantly composite attachments on teeth often used during aligner therapy, for enhanced control, risk fracture. This would delay treatment and possibly damage the enamel.

Advantageously, the presently disclosed dental aligner removal tool 100 reduces contact of the tool 100 with the tooth T itself by providing at least two points of contact at which the removal tool 100 contacts the aligner A such that when a pivoting force is applied against the aligner A the forces are primarily directed to the aligner A itself as opposed to the underlying tooth, thereby minimizing discomfort and/or potential damage to the tooth.

Figure 4:
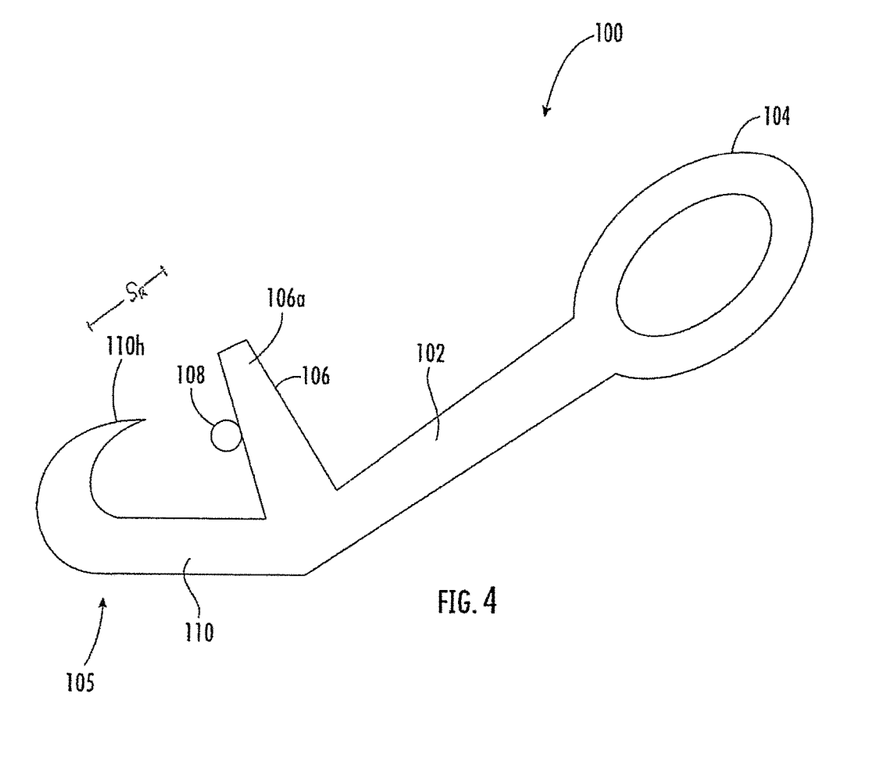
FIG. 4 is a front view of a dental aligner removal tool in accordance with the present disclosure.

In particular, as shown in FIG. 4, a dental aligner removal tool 100 may include an elongated arm 102 including a gripping member, which may be a ring 104, that is disposed at a proximal end thereof and an aligner gripping member 105 at a distal end thereof. The ring 104 may include a hold 104h which may be configured to receive a finger therethrough to facilitate manipulation of the tool 100. The aligner gripping member 105 may include a first member 106 extending generally longitudinally and orthogonally relative to the elongated arm 102 and a second member 110 that defines a hook and that extends from a distal end of the elongated arm 102 and curves proximally toward the first member 106. Distal ends of the first and the second members 106 and 110 may define a space therebetween.

Further, a protrusion 108 which may be a bulbous extension from the first member 106 may be disposed on the first member 106 along a distal section thereof and serves as a contact point that may be configured to apply a force to a lateral surface of the aligner A. The protrusion 108 may be of any shape. The second member 110 may have a tapered distal end 110h. The tapered distal end 110h, a distal section 106a of the first member 106 and the protrusion 108 may each be configured to cooperate with one another for removing a dental aligner and are configured to be a contact point abutting the dental aligner during removal, thereby providing a stable pivot or purchase point for securely positioning the first member 106 against the biting surface $A_B$ of the aligner A. Advantageously, during removal of the aligner, all the forces are applied to the aligner itself as opposed to requiring that forces be applied to a tooth surface as is conventional. This means that much less, if any force, is applied against the tooth surface during removal when using the dental aligner removal tool 100.

Figure 5:
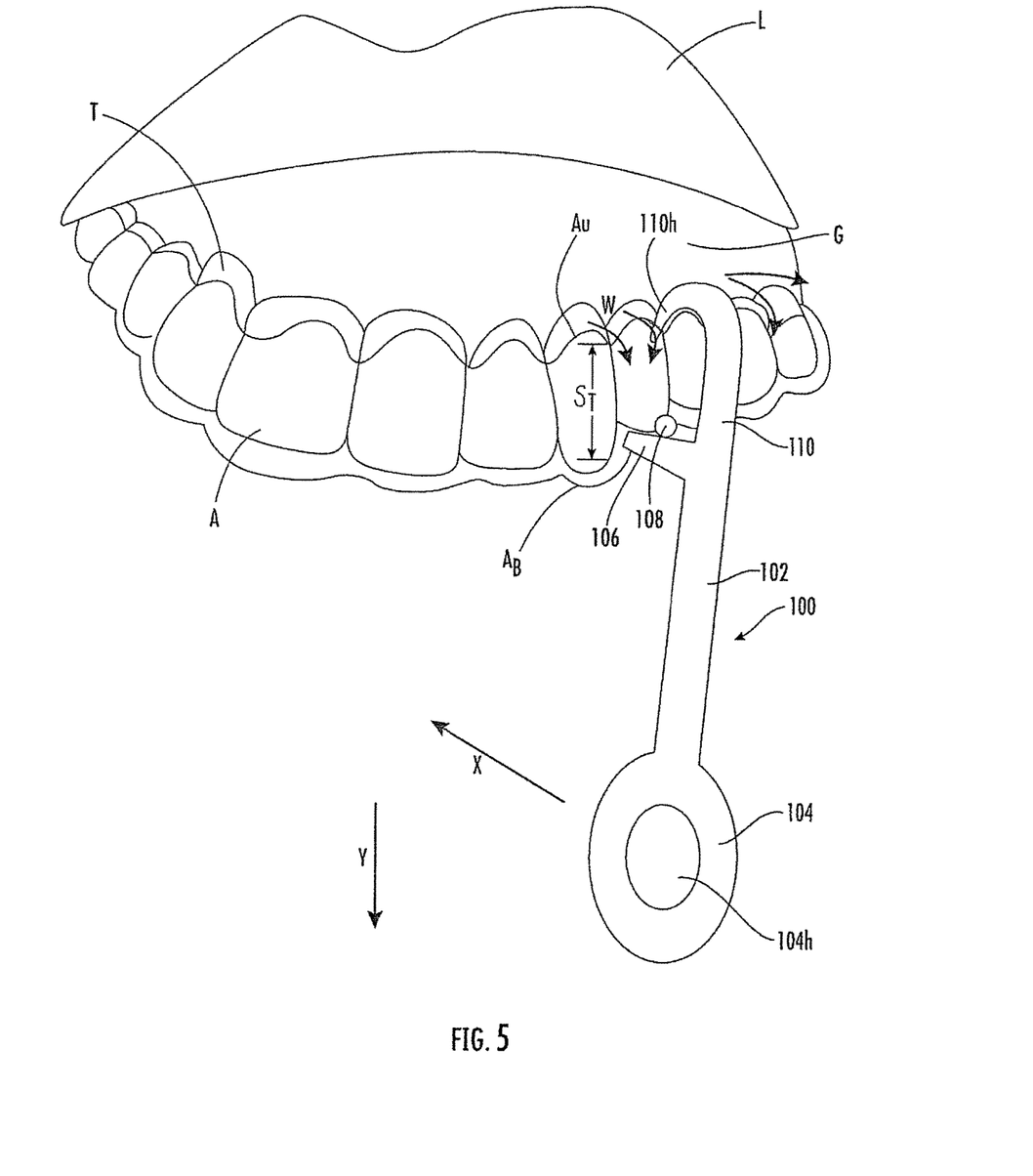
FIG. 5 illustrates the dental aligner removal tool of FIG. 3 shown in use.
Figure 6:
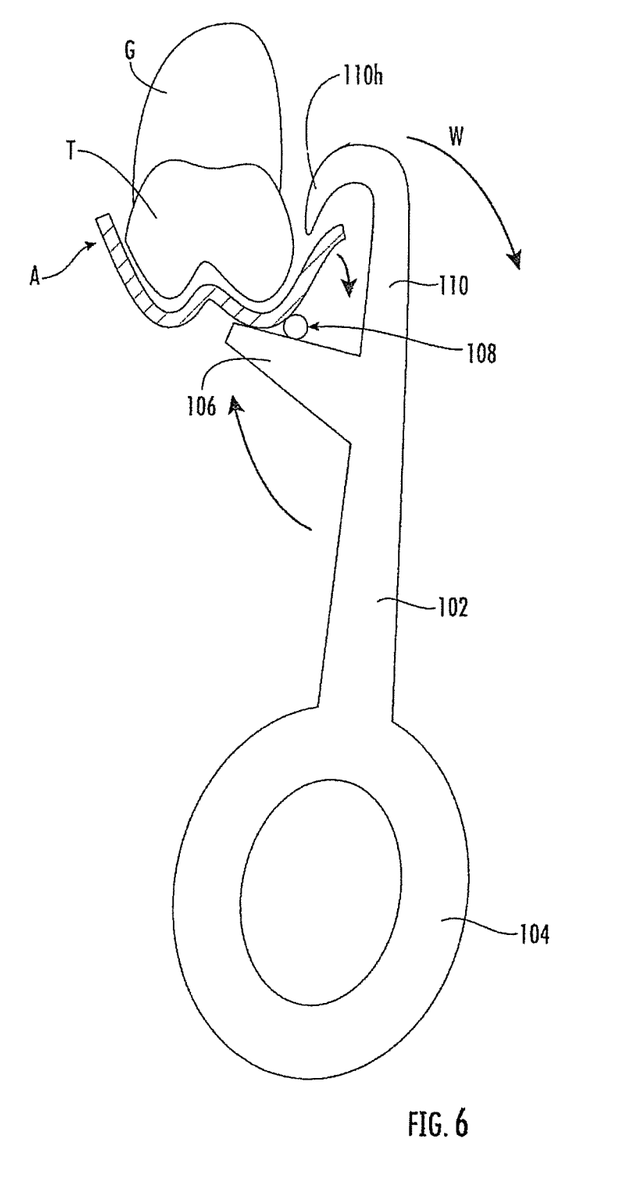
FIG. 6 is a cross-sectional view of a dental aligner being removed from a tooth with the dental aligner removal tool of FIG. 4.

Use of the dental aligner removal tool 100 will now be described with reference to FIGS. 5 and 6. As shown in FIGS. 5-6, the tool 100 defines a space $S_R$ between the distal end or hook end 110h and the first member 106. The space $S_R$ may be dimensioned to correspond to a length $S_T$ of the tooth T or aligner A (which should have similar dimensions as the tooth) such that gumline and biting surfaces $A_U$ and $A_B$ of the aligner A may be positioned between the first member 106 and the distal end or hook end 110h. Protrusion 108 may maintain such positioning of the aligner A within the space $S_R$ defined by the tool 100.

The tool 100 may be placed with the distal end 110h of the second member 110 against a gumline portion of the aligner A which is closest to the gumline G and the first member 106 is placed against a biting surface of the aligner A that against a biting surface of the tooth T such that the tool 100 contacts the aligner A at the distal end 110h, at the protrusion 108 and at the first member 106. Once so positioned, the tool 100 may be moved as indicated by directional arrow X which causes the aligner A to rotate off froth the tooth surface along directional arrows W. Thereafter, the tool 100 may be pulled along directional arrow Y to fully remove the aligner A away from the teeth T.

During the removal of the aligner A, the tool 100 thus includes a contact point at the distal end 110h which is where the aligner A would meet the gumline G when secured to the teeth T and will also contact the biting surfaces of the teeth, i.e., near the chewing surfaces of the teeth T, with the first member 106. The protrusion 108 facilitates maintaining the aligner A positioned along a distal section of the first arm 106 while applying a pivoting force as the tool 100 is rotated along directional arrow J.

Thus, as shown best in FIG. 6, the aligner A is forced to flex away from the tooth surface $T_S$ thereby causing the suction between the tooth T and the aligner A to be reduced to facilitate removal of the aligner A. Importantly, the forces are directed to the contact point between the aligner A and the first member 106 as opposed to directing forces against the tooth T or other structures within the mouth. Further, by maintaining contact between the first member 106 and the aligner A, the tool 100 is not permitted to slide. In other words, the distal end or hook end 110h is maintained at the gumline end $A_U$ of the aligner A such that the hook end 110h is less likely to enter between the aligner A and the tooth surface Ts and the potential of damage to the tooth surface Ts or surrounding tissue is therefore reduced. During use, the contact point of the aligner A and the protrusion 108 may initially remain fixed and the hook 110h may rotate relative to that contact point, thereby causing separation of the aligner A from the tooth surface Ts.

The removal tool 100 may be formed from any suitable material having sufficient rigidity, for example, to permit the tool 100 to cause a torque force upon the aligner A when the tool is engaged with the aligner A. Such materials may include, for example, a metal or a polymeric material such as a plastic or an elastic material such as a rubber or rubber like material that while substantially rigid may be capable of small deflections. Further, the thickness of the tool 100 and its constituent elements including, for example, first member 106 and second member 110 may have a sufficient material strength, thickness and/or configuration such that the tool 100 does not fail or substantially deform during use while forces are exerted upon it. As shown in FIG. 2, the first member 106 may be wedge or triangular shaped such that when a force is applied to the first member 106, the first member 106 will be less prone to bend relative to the elongated arm 102 as its triangular shape would transfer the forces in such a away as to make it more rigid even under the application of external forces.

Further, the material forming the tool 100 may include a coating, on at least a portion thereof (e.g., first and the second members 106 and 110) that are more prone to contact the patient. The coating may be, for example, a rubberized coating to facilitate greater grip of the tool 100 or to minimize discomfort to the patient during use if the tool 100 inadvertently touches any soft tissue within the patient's mouth. In an embodiment, the end 110*h* of the hook may be rubberized such that it does not include a sharp end and may me capable of being flexed or deformed to an extent. Additionally or alternatively, at least a portion of the elongated arm 102 and/or the gripping member 104 may be rubberized and/or textured to facilitate an improved grip of the tool 100 by the dentist or technician.

Having described at least one of the preferred embodiments of the present disclosure with reference to the accompanying drawings, it is to be understood that such embodiments are merely exemplary and that the disclosure is not limited to those precise embodiments, and that various changes, modifications, and adaptations may be effected therein by one skilled in the art without departing from the scope or spirit of the disclosure as defined in the appended claims. The scope of the disclosure, therefore, shall be defined solely by the following claims. Further, it will be apparent to those of skill in the art that numerous changes may be made in such details without departing from the spirit and the principles of the disclosure. It should be appreciated that the present disclosure is capable of being embodied in other forms without departing from its essential characteristics.

What is claimed is:

1. A dental tool for removing a dental aligner secured to teeth, comprising:
    an elongated arm;
    a generally C-shaped member disposed at a distal end of the elongated arm, the generally C-shaped member including:
    a first member extending generally orthogonally relative to the elongated arm having a distal end; and
    a second member spaced apart from the first member, the first member defining a first contact surface that is configured to contact a biting surface of the aligner, a distal end of the second member defining a second contact surface that is configured to contact a gumline end of the dental aligner; and
    a protrusion extending from and disposed along the first member, the protrusion defining a third contact surface that is configured to contact a lateral surface of the aligner,
    wherein each of the first, second, third contact surfaces are configured to simultaneously contact the dental aligner at three discrete points on the dental aligner such that when the first, second, and third contact surfaces engage the dental aligner, contact between the aligner and the first, second, and third contact surfaces is maintained as the dental aligner is being removed from the teeth, and wherein each of the first, second, third contact surfaces define a discrete point on the dental tool.

2. The dental tool according to claim 1, wherein:
    the protrusion is configured to stabilize and maintain a biting surface end of the dental aligner on the first member, the first member and the second member defines a space therebetween to receive a width of the dental aligner corresponding to a length of a tooth when the dental aligner is secured to the tooth; and
    wherein when the dental aligner is disposed within the space defined between the first and second members, pivoting of the elongated arm causes the distal end of the second member to exert a flexing force upon a gumline end of the aligner relative to a biting surface end of the aligner, thereby causing the aligner to separate from the teeth.

3. The dental tool of claim 2, wherein the second member defines a hook curving toward the first member.

4. The dental tool of claim 2, wherein the tool includes a rubberized surface to facilitate improved grip.

5. The dental tool of claim 2, wherein the distal end of the second member is rubberized.

6. The dental tool of claim 1, wherein: the third contact point is configured to contact a biting end surface of the aligner and the third contact point is configured to inhibit slipping of the first member relative to the biting end surface of the aligner by being configured to apply a force to the lateral surface of the aligner, and the second contact point is configured to engage the aligner to exert a flexing force upon the aligner when the elongated arm is pivoted relative to the third contact point.

7. The dental tool of claim 6, further comprising a gripping member at a proximal end of the elongated arm.

8. The dental tool of claim 7, wherein the gripping member is a ring.

9. A method of removing a dental aligner secured to teeth, comprising:
    a dental tool for removing a dental aligner secured to teeth, comprising:
        an elongated arm;
        a generally C-shaped member disposed at a distal end of the elongated arm, the generally C-shaped member including:
        a first member extending generally orthogonally relative to the elongated arm having a distal end; and
        a second member spaced apart from the first member, the first member defining a first contact surface that is configured to contact a biting surface of the aligner, a distal end of the second member defining a second contact surface that is configured to contact a gumline end of the dental aligner; and
        a protrusion extending from and disposed along the first member, the protrusion defining a third contact surface that is configured to contact a lateral surface of the aligner;
    positioning the dental tool such that the first contact surface contacts the biting surface of the aligner, the second contact surface contacts the gumline end of the aligner, and the third contact point contacts the lateral surface of the aligner; and
    pivoting the dental tool such that the second contact point rotates with respect to the third contact point;
    wherein each of the first, second, third contact surfaces are configured to simultaneously contact the dental aligner at three discrete points on the dental aligner such that when the first, second, and third contact surfaces engage the dental aligner, contact between the aligner and the first, second, and third contact surfaces is maintained as the dental aligner is being removed from the teeth and wherein each of the first, second, third contact surfaces define a discrete point on the dental tool.

10. The method of claim 9, further comprising, after the step of pivoting, pulling the aligner in a direction extending generally along a lateral surface of the teeth away from a gumline of a patient's mouth.

11. The method of claim 9, wherein:
    wherein when the dental aligner is disposed within the space defined between the first and second members, pivoting of the elongated arm causes a distal end of the second member to exert a flexing force upon a gumline end of the aligner relative to a biting surface end of the aligner, thereby causing the aligner to separate from the teeth.

12. The dental tool of claim 11, wherein the second member defines a hook curving toward the first member.

13. The method of claim 11, wherein the tool exerts a flexing force that is concentrated on the aligner and any force upon any surrounding mouth structure is minimized.

14. The method of claim 11, wherein the dental tool further comprises:
   a gripping member at a proximal end of the elongated arm.

15. The method of claim 14, wherein the gripping member is a ring.

16. The method of claim 15, wherein during use, a finger is receivable within the ring.

17. The method of claim 9, wherein the tool includes a rubberized surface to facilitate improved grip.

18. The method of claim 9, wherein at least one of the first, second, and third contact surfaces is rubberized.

19. A dental tool for removing a dental aligner secured to teeth, comprising:
   an elongated arm extending in a generally longitudinal direction;
   a generally C-shaped member disposed at a distal end of the elongated arm, the generally C-shaped member including a first member extending generally orthogonally relative to the elongated arm having a distal end and a second member spaced apart from the first member;
   a protrusion extending from and disposed along the first member, the protrusion being configured to stabilize and maintain a biting surface end of the dental aligner on the first member, the first member and the second member defining a space therebetween to receive a width of the dental aligner corresponding to a length of a tooth when the dental aligner is secured to the tooth;
   wherein when the dental aligner is disposed within the space defined between the first and second members, pivoting of the elongated arm causes the distal end of the second member to exert a flexing force upon a gumline end of the aligner relative to a biting surface end of the aligner, thereby causing the aligner to separate from the teeth; and
   wherein the first member defines the first contact surface, a distal end of the second member defines a second contact surface, the protrusion defines the third contact surface, the first contact surface and the third contact surface being configured to contact a biting end surface of the aligner, the second contact surface being configured to contact a gumline end of the aligner, the third contact surface being configured to inhibit slipping of the first member relative to the biting end surface of the aligner by being configured to apply a force to a lateral surface of the aligner, the second contact surface being configured to engage the aligner to exert a flexing force upon the aligner when the elongated arm is pivoted relative to the third contact surface.

20. A dental tool for removing a dental aligner secured to teeth, comprising:
   an arm member configured to be grasped by a technician;
   a removal member disposed at a distal end of the stabilizing arm, the removal member comprising:
      a first contact surface configured to contact a biting surface of the dental aligner during use;
      a second contact surface configured to contact a gumline end of the dental aligner during use; and
      a stopping contact surface positioned adjacent to the first contact surface, the stopping contact surface configured to contact a lateral side of the dental aligner and to prevent slipping of the dental aligner relative to a length of the second contact surface during use such that during use, the first contact surface, the second contact surface, and the stopping contact surface contact simultaneously contact the dental aligner at three points such that rotation of a proximal end the arm member relative to the distal end imparts a force upon the three points to effect removal of the dental aligner from the teeth.

* * * * *